US009113838B2

(12) United States Patent
Tesfayesus et al.

(10) Patent No.: US 9,113,838 B2
(45) Date of Patent: *Aug. 25, 2015

(54) SCREENING DEVICES AND METHODS FOR OBSTRUCTIVE SLEEP APNEA THERAPY

(71) Applicant: Cyberonics, Inc., Houston, TX (US)

(72) Inventors: Wondimeneh Tesfayesus, St. Paul, MN (US); Stephen L. Bolea, Watertown, MN (US); Peter R. Eastwood, Western Australia (AU); David R. Hillman, Western Australia (AU)

(73) Assignee: CYBERONICS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,130

(22) Filed: Sep. 2, 2014

(65) Prior Publication Data

US 2015/0005642 A1 Jan. 1, 2015

Related U.S. Application Data

(63) Continuation of application No. 13/205,315, filed on Aug. 8, 2011, now Pat. No. 8,855,771, which is a continuation of application No. 13/113,524, filed on May 23, 2011, now abandoned.

(60) Provisional application No. 61/467,758, filed on Mar. 25, 2011, provisional application No. 61/437,573, filed on Jan. 28, 2011.

(51) Int. Cl.
*A61N 1/00* (2006.01)
*A61B 1/267* (2006.01)
(Continued)

(52) U.S. Cl.
CPC ............... *A61B 1/267* (2013.01); *A61B 1/233* (2013.01); *A61B 5/4552* (2013.01); *A61N 1/0519* (2013.01); *A61N 1/3611* (2013.01)

(58) Field of Classification Search
CPC .......... A61B 1/233; A61B 1/24; A61B 1/267; A61B 5/4552; A61B 5/4542; A61N 1/0519; A61N 1/3611
See application file for complete search history.

(56) References Cited

U.S. PATENT DOCUMENTS 758,030 A 4/1904 Carence
1,520,930 A 12/1924 Calhoun
(Continued)

FOREIGN PATENT DOCUMENTS

EP 0 892 926 B1 6/2002
EP 0 900 102 B1 7/2004
(Continued)

OTHER PUBLICATIONS

Spence et al., "High-flow nasal cannula as a device to provide continuous positive airway pressure in infants," *Journal of Perinatology*, Dec. 2007, pp. 772-775, vol. 27 (12), Nature Publishing Group.
(Continued)

*Primary Examiner* — George Manuel

(57) ABSTRACT

Devices and methods for treating obstructive sleep apnea by first performing an assessment of the patient that involves observing the patient's upper airway during a tongue protrusion maneuver. The assessment may, for example, be done using endoscopy to observe the upper airway while the patient is awake in the supine position. An adequate response of the upper airway during the tongue protrusion maneuver is indicative of likely therapeutic success with hypoglossal nerve stimulation, and may be used for making clinical decisions. The principles of the present invention may be applied to other therapeutic interventions for OSA involving the upper airway.

20 Claims, 8 Drawing Sheets

(51) Int. Cl.
   *A61B 1/233*  (2006.01)
   *A61N 1/05*   (2006.01)
   *A61N 1/36*   (2006.01)
   *A61B 5/00*   (2006.01)

(56) References Cited

U.S. PATENT DOCUMENTS

| | | | |
|---|---|---|---|
| 1,701,277 A | 2/1929 | Shindel |
| 1,914,418 A | 6/1933 | Goyena |
| 2,046,664 A | 7/1936 | Weaver |
| 2,151,227 A | 3/1939 | Pawelek |
| 2,237,954 A | 4/1941 | Wilson |
| 2,243,360 A | 5/1941 | Slatis |
| 2,274,886 A | 3/1942 | Carroll |
| 2,526,586 A | 10/1950 | Shuff |
| 2,693,799 A | 11/1954 | Herman |
| 2,777,442 A | 1/1957 | Zelano |
| 2,928,388 A | 3/1960 | Jaroslaw |
| 3,457,917 A | 7/1969 | Mercurio |
| 3,513,839 A | 5/1970 | Vacante |
| 3,680,555 A | 8/1972 | Warncke |
| 3,722,509 A | 3/1973 | Nebel |
| 3,774,618 A | 11/1973 | Avery |
| 3,865,106 A | 2/1975 | Palush |
| 3,884,223 A | 5/1975 | Keindl |
| 3,906,936 A | 9/1975 | Habal |
| 4,220,150 A | 9/1980 | King |
| 4,221,217 A | 9/1980 | Amezcua |
| 4,267,831 A | 5/1981 | Aguilar |
| 4,374,527 A | 2/1983 | Iversen |
| 4,567,892 A | 2/1986 | Plicchi et al. |
| 4,573,481 A | 3/1986 | Bullara |
| 4,777,963 A | 10/1988 | McKenna |
| 4,830,008 A | 5/1989 | Meer |
| 4,899,750 A | 2/1990 | Ekwall |
| 4,915,105 A | 4/1990 | Lee |
| 4,919,136 A | 4/1990 | Alt |
| 4,940,065 A | 7/1990 | Tanagho et al. |
| 4,960,133 A | 10/1990 | Hewson |
| 4,996,983 A | 3/1991 | AmRhein |
| 5,016,808 A | 5/1991 | Heil, Jr. et al. |
| 5,105,826 A | 4/1992 | Smits et al. |
| 5,121,754 A | 6/1992 | Mullett |
| 5,133,354 A | 7/1992 | Kallok |
| 5,146,918 A | 9/1992 | Kallok et al. |
| 5,158,080 A | 10/1992 | Kallok |
| 5,174,287 A | 12/1992 | Kallok et al. |
| 5,178,156 A | 1/1993 | Takishima et al. |
| 5,190,053 A | 3/1993 | Meer |
| 5,211,173 A | 5/1993 | Kallok et al. |
| 5,215,082 A | 6/1993 | Kallok et al. |
| 5,277,193 A | 1/1994 | Takishima et al. |
| 5,281,219 A | 1/1994 | Kallok et al. |
| 5,300,094 A | 4/1994 | Kallok et al. |
| 5,324,321 A | 6/1994 | Pohndorf et al. |
| 5,335,657 A | 8/1994 | Terry, Jr. et al. |
| 5,344,438 A | 9/1994 | Testerman et al. |
| 5,388,578 A | 2/1995 | Yomtov et al. |
| 5,392,773 A | 2/1995 | Bertrand |
| 5,417,205 A | 5/1995 | Wang |
| 5,425,359 A | 6/1995 | Liou |
| 5,458,629 A | 10/1995 | Baudino et al. |
| 5,483,969 A | 1/1996 | Testerman et al. |
| 5,485,836 A | 1/1996 | Lincoln |
| 5,485,851 A | 1/1996 | Erickson |
| 5,511,543 A | 4/1996 | Shirley |
| 5,522,382 A | 6/1996 | Sullivan et al. |
| 5,522,862 A | 6/1996 | Testerman et al. |
| 5,531,778 A | 7/1996 | Maschino et al. |
| 5,540,732 A | 7/1996 | Testerman |
| 5,540,733 A | 7/1996 | Testerman et al. |
| 5,540,734 A | 7/1996 | Zabara |
| 5,546,938 A | 8/1996 | McKenzie |
| 5,549,655 A | 8/1996 | Erickson |
| 5,568,808 A | 10/1996 | Rimkus |
| 5,591,216 A | 1/1997 | Testerman et al. |
| 5,630,411 A | 5/1997 | Holscher |
| 5,682,881 A | 11/1997 | Winthrop et al. |
| 5,697,105 A | 12/1997 | White |
| 5,697,363 A | 12/1997 | Hart |
| 5,730,122 A | 3/1998 | Lurie |
| 5,740,798 A | 4/1998 | McKinney |
| 5,752,511 A | 5/1998 | Simmons et al. |
| 5,787,884 A | 8/1998 | Tovey |
| 5,826,579 A * | 10/1998 | Remmers et al. ............. 128/848 |
| 5,848,589 A | 12/1998 | Welnetz |
| 5,855,552 A | 1/1999 | Houser et al. |
| 5,890,491 A | 4/1999 | Rimkus |
| 5,895,360 A | 4/1999 | Christopherson et al. |
| 5,922,014 A | 7/1999 | Warman et al. |
| 5,938,596 A | 8/1999 | Woloszko et al. |
| 5,944,680 A | 8/1999 | Christopherson et al. |
| 5,947,119 A | 9/1999 | Reznick |
| 6,010,459 A | 1/2000 | Silkoff et al. |
| 6,015,389 A | 1/2000 | Brown |
| 6,021,352 A | 2/2000 | Christopherson et al. |
| 6,021,354 A | 2/2000 | Warman et al. |
| 6,029,667 A | 2/2000 | Lurie |
| 6,041,780 A | 3/2000 | Richard |
| 6,066,165 A | 5/2000 | Racz |
| 6,098,624 A | 8/2000 | Utamaru |
| 6,109,262 A | 8/2000 | Tovey |
| 6,119,690 A | 9/2000 | Pantaleo |
| 6,126,611 A | 10/2000 | Bourgeois et al. |
| 6,132,384 A | 10/2000 | Christopherson et al. |
| 6,198,970 B1 | 3/2001 | Freed et al. |
| 6,201,994 B1 | 3/2001 | Warman et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,240,316 B1 | 5/2001 | Richmond et al. |
| 6,244,267 B1 | 6/2001 | Eifrig |
| 6,251,126 B1 | 6/2001 | Ottenhoff et al. |
| 6,269,269 B1 | 7/2001 | Ottenhoff et al. |
| 6,345,202 B2 | 2/2002 | Richmond et al. |
| 6,366,815 B1 | 4/2002 | Haugland et al. |
| 6,460,539 B1 | 10/2002 | Japuntich et al. |
| 6,484,725 B1 | 11/2002 | Chi |
| 6,511,458 B2 | 1/2003 | Milo et al. |
| 6,514,217 B1 | 2/2003 | Selmon et al. |
| 6,542,776 B1 | 4/2003 | Gordon et al. |
| 6,561,188 B1 | 5/2003 | Ellis |
| 6,587,725 B1 | 7/2003 | Durand et al. |
| 6,600,956 B2 | 7/2003 | Maschino et al. |
| 6,606,521 B2 | 8/2003 | Paspa et al. |
| 6,626,179 B1 | 9/2003 | Pedley |
| 6,636,767 B1 | 10/2003 | Knudson et al. |
| 6,641,542 B2 | 11/2003 | Cho et al. |
| 6,647,289 B2 | 11/2003 | Prutchi |
| 6,651,652 B1 | 11/2003 | Ward |
| 6,718,982 B2 | 4/2004 | Smith et al. |
| 6,719,725 B2 | 4/2004 | Milo et al. |
| 6,721,603 B2 | 4/2004 | Zabara et al. |
| 6,772,015 B2 | 8/2004 | Dahl et al. |
| 6,776,162 B2 | 8/2004 | Wood |
| 6,799,575 B1 | 10/2004 | Carter |
| 6,819,958 B2 | 11/2004 | Weiner et al. |
| 6,829,503 B2 | 12/2004 | Alt |
| 6,829,508 B2 | 12/2004 | Schulman et al. |
| RE38,705 E | 2/2005 | Hill et al. |
| 6,876,885 B2 | 4/2005 | Swoyer et al. |
| 6,881,192 B1 | 4/2005 | Park |
| 6,883,518 B2 | 4/2005 | Mittelstadt et al. |
| 6,890,306 B2 | 5/2005 | Poezevera |
| 6,904,320 B2 | 6/2005 | Park et al. |
| 6,907,295 B2 | 6/2005 | Gross et al. |
| 6,928,324 B2 | 8/2005 | Park et al. |
| 6,978,171 B2 | 12/2005 | Goetz et al. |
| 6,997,177 B2 | 2/2006 | Wood |
| 7,027,869 B2 | 4/2006 | Danek et al. |
| 7,054,692 B1 | 5/2006 | Whitehurst et al. |
| 7,065,410 B2 | 6/2006 | Bardy et al. |
| 7,082,331 B1 | 7/2006 | Park et al. |
| 7,087,053 B2 | 8/2006 | Vanney |

(56) References Cited

U.S. PATENT DOCUMENTS

| | | |
|---|---|---|
| 7,089,932 B2 | 8/2006 | Dodds |
| 7,094,206 B2 | 8/2006 | Hoffman |
| 7,117,036 B2 | 10/2006 | Florio |
| 7,128,717 B1 | 10/2006 | Thach et al. |
| 7,142,919 B2 | 11/2006 | Hine et al. |
| 7,149,573 B2 | 12/2006 | Wang |
| 7,152,604 B2 | 12/2006 | Hickle et al. |
| 7,155,278 B2 | 12/2006 | King et al. |
| 7,156,098 B2 | 1/2007 | Dolezal et al. |
| 7,160,252 B2 | 1/2007 | Cho |
| 7,160,255 B2 | 1/2007 | Saadat |
| 7,178,524 B2 | 2/2007 | Noble |
| 7,200,440 B2 | 4/2007 | Kim et al. |
| 7,225,034 B2 | 5/2007 | Ries et al. |
| 7,239,918 B2 | 7/2007 | Strother et al. |
| 7,242,987 B2 | 7/2007 | Holleman et al. |
| 7,277,749 B2 | 10/2007 | Gordon et al. |
| 7,283,867 B2 | 10/2007 | Strother et al. |
| 7,302,951 B2 | 12/2007 | Mittelstadt et al. |
| 7,313,442 B2 | 12/2007 | Velasco et al. |
| 7,346,398 B2 | 3/2008 | Gross et al. |
| 7,366,572 B2 | 4/2008 | Heruth et al. |
| 7,396,333 B2 | 7/2008 | Stahmann et al. |
| 7,438,686 B2 | 10/2008 | Cho et al. |
| 7,463,928 B2 | 12/2008 | Lee et al. |
| 7,473,227 B2 | 1/2009 | Hsu et al. |
| 7,515,968 B2 | 4/2009 | Metzler et al. |
| 7,524,292 B2 | 4/2009 | Cho et al. |
| 7,561,922 B2 | 7/2009 | Cohen et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,627,375 B2 | 12/2009 | Bardy et al. |
| 7,630,771 B2 | 12/2009 | Cauller |
| 7,634,315 B2 | 12/2009 | Cholette |
| 7,636,602 B2 | 12/2009 | Baru Fassio et al. |
| 7,657,311 B2 | 2/2010 | Bardy et al. |
| 7,660,632 B2 | 2/2010 | Kirby et al. |
| 7,662,105 B2 | 2/2010 | Hatlestad |
| 7,672,728 B2 | 3/2010 | Libbus et al. |
| 7,672,729 B2 | 3/2010 | Koh et al. |
| 7,680,537 B2 | 3/2010 | Stahmann et al. |
| 7,680,538 B2 | 3/2010 | Durand et al. |
| 7,684,869 B2 | 3/2010 | Bradley et al. |
| 7,697,968 B2 | 4/2010 | Moore |
| 7,697,984 B2 | 4/2010 | Hill et al. |
| 7,697,990 B2 | 4/2010 | Ujhazy et al. |
| 7,717,848 B2 | 5/2010 | Heruth et al. |
| 7,720,534 B2 | 5/2010 | Bardy et al. |
| 7,725,195 B2 | 5/2010 | Lima et al. |
| 7,725,198 B2 | 5/2010 | Cross, Jr. et al. |
| 7,734,340 B2 | 6/2010 | De Ridder |
| 7,734,348 B2 | 6/2010 | Zhang et al. |
| 7,738,952 B2 | 6/2010 | Yun et al. |
| 7,747,323 B2 | 6/2010 | Libbus et al. |
| 7,751,880 B1 | 7/2010 | Cholette |
| 7,751,885 B2 | 7/2010 | Bardy et al. |
| 7,758,384 B2 | 7/2010 | Alexander et al. |
| 7,765,000 B2 | 7/2010 | Zhang et al. |
| 7,769,461 B2 | 8/2010 | Whitehurst et al. |
| 7,783,353 B2 | 8/2010 | Libbus et al. |
| 7,785,262 B2 | 8/2010 | Melker et al. |
| 7,787,959 B1 | 8/2010 | Morgan |
| 7,792,590 B1 | 9/2010 | Pianca et al. |
| 7,797,050 B2 | 9/2010 | Libbus et al. |
| 7,797,057 B2 | 9/2010 | Harris |
| 7,797,058 B2 | 9/2010 | Mrva et al. |
| 7,805,195 B2 | 9/2010 | Zealear |
| 7,809,442 B2 | 10/2010 | Bolea et al. |
| 7,813,797 B2 | 10/2010 | Bardy et al. |
| 7,813,802 B2 | 10/2010 | Tcheng et al. |
| 7,813,809 B2 | 10/2010 | Strother et al. |
| 7,818,063 B2 | 10/2010 | Wallace et al. |
| 7,822,486 B2 | 10/2010 | Foster et al. |
| 8,249,723 B2 | 8/2012 | McCreery |
| 8,386,046 B2 | 2/2013 | Tesfayesus et al. |
| 2001/0010010 A1 | 7/2001 | Richmond et al. |
| 2001/0031929 A1 | 10/2001 | O'Toole |
| 2002/0010495 A1 | 1/2002 | Freed et al. |
| 2002/0049479 A1 | 4/2002 | Pitts |
| 2002/0092527 A1 | 7/2002 | Wood |
| 2002/0128700 A1 | 9/2002 | Cross |
| 2002/0166556 A1 | 11/2002 | Jacob |
| 2002/0195108 A1 | 12/2002 | Mittelstadt et al. |
| 2002/0195109 A1 | 12/2002 | Mittelstadt et al. |
| 2003/0034031 A1 | 2/2003 | Lev et al. |
| 2003/0083696 A1 | 5/2003 | Avital |
| 2003/0093128 A1 | 5/2003 | Freed et al. |
| 2003/0106555 A1 | 6/2003 | Tovey |
| 2003/0106556 A1 | 6/2003 | Alperovich et al. |
| 2003/0114895 A1 | 6/2003 | Gordon et al. |
| 2003/0114905 A1 | 6/2003 | Kuzma |
| 2003/0167018 A1 | 9/2003 | Wyckoff |
| 2003/0195571 A1 | 10/2003 | Burnes et al. |
| 2003/0209145 A1 | 11/2003 | Soper |
| 2003/0216789 A1 | 11/2003 | Deem et al. |
| 2004/0015204 A1 | 1/2004 | Whitehurst et al. |
| 2004/0020489 A1 | 2/2004 | Gillispie et al. |
| 2004/0049241 A1 | 3/2004 | Campos |
| 2004/0055603 A1 | 3/2004 | Bruce |
| 2004/0073272 A1 | 4/2004 | Knudson et al. |
| 2004/0089303 A1 | 5/2004 | Chien |
| 2004/0111139 A1 | 6/2004 | McCreery |
| 2004/0116819 A1 | 6/2004 | Alt |
| 2004/0162499 A1 | 8/2004 | Nagai et al. |
| 2004/0194784 A1 | 10/2004 | Bertrand |
| 2004/0215288 A1 | 10/2004 | Lee et al. |
| 2004/0230278 A1 | 11/2004 | Dahl et al. |
| 2004/0233058 A1 | 11/2004 | Dodds |
| 2004/0260310 A1 | 12/2004 | Harris |
| 2004/0261791 A1 | 12/2004 | Horian |
| 2005/0004610 A1 | 1/2005 | Kim et al. |
| 2005/0010265 A1 | 1/2005 | Fassio et al. |
| 2005/0038490 A1 | 2/2005 | Gross et al. |
| 2005/0039757 A1 | 2/2005 | Wood |
| 2005/0043644 A1 | 2/2005 | Stahmann et al. |
| 2005/0043772 A1 | 2/2005 | Stahmann et al. |
| 2005/0076908 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0098176 A1 | 5/2005 | Hoffrichter |
| 2005/0101833 A1 | 5/2005 | Hsu et al. |
| 2005/0119711 A1 | 6/2005 | Cho et al. |
| 2005/0139216 A1 | 6/2005 | Mittelstadt et al. |
| 2005/0165457 A1 | 7/2005 | Benser et al. |
| 2005/0209513 A1 | 9/2005 | Heruth et al. |
| 2005/0209643 A1 | 9/2005 | Heruth et al. |
| 2005/0234523 A1 | 10/2005 | Levin et al. |
| 2005/0235992 A1 | 10/2005 | Djupesland |
| 2005/0240241 A1 | 10/2005 | Yun et al. |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0005842 A1 | 1/2006 | Rashad et al. |
| 2006/0025828 A1 | 2/2006 | Armstrong et al. |
| 2006/0030919 A1 | 2/2006 | Mrva et al. |
| 2006/0032497 A1 | 2/2006 | Doshi |
| 2006/0052836 A1 | 3/2006 | Kim et al. |
| 2006/0058588 A1 | 3/2006 | Zdeblick |
| 2006/0058852 A1 | 3/2006 | Koh et al. |
| 2006/0064029 A1 | 3/2006 | Arad |
| 2006/0064138 A1 | 3/2006 | Velasco et al. |
| 2006/0079802 A1 | 4/2006 | Jensen et al. |
| 2006/0095088 A1 | 5/2006 | De Ridder |
| 2006/0111755 A1 | 5/2006 | Stone et al. |
| 2006/0116739 A1 | 6/2006 | Betser et al. |
| 2006/0129189 A1 | 6/2006 | George et al. |

(56) References Cited

U.S. PATENT DOCUMENTS

| | | |
|---|---|---|
| 2006/0135886 A1 | 6/2006 | Lippert et al. |
| 2006/0136024 A1 | 6/2006 | Cohen et al. |
| 2006/0142815 A1 | 6/2006 | Tehrani et al. |
| 2006/0144398 A1 | 7/2006 | Doshi et al. |
| 2006/0150978 A1 | 7/2006 | Doshi et al. |
| 2006/0150979 A1 | 7/2006 | Doshi et al. |
| 2006/0150980 A1 | 7/2006 | Kim |
| 2006/0167497 A1 | 7/2006 | Armstrong et al. |
| 2006/0184204 A1 | 8/2006 | He |
| 2006/0195170 A1 | 8/2006 | Cohen et al. |
| 2006/0211951 A1 | 9/2006 | Milajasevic et al. |
| 2006/0224209 A1 | 10/2006 | Meyer |
| 2006/0224211 A1 | 10/2006 | Durand |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271118 A1 | 11/2006 | Libbus et al. |
| 2006/0271137 A1 | 11/2006 | Stanton-Hicks |
| 2006/0282127 A1 | 12/2006 | Zealear |
| 2006/0293720 A1 | 12/2006 | DiLorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0043411 A1 | 2/2007 | Foster et al. |
| 2007/0095347 A1 | 5/2007 | Lampotang et al. |
| 2007/0125379 A1 | 6/2007 | Pierro et al. |
| 2007/0175478 A1 | 8/2007 | Brunst |
| 2007/0227542 A1 | 10/2007 | Kashmakov et al. |
| 2007/0277832 A1 | 12/2007 | Doshi et al. |
| 2007/0283692 A1 | 12/2007 | Tetsuka et al. |
| 2007/0283962 A1 | 12/2007 | Doshi et al. |
| 2007/0295338 A1 | 12/2007 | Loomas et al. |
| 2008/0023007 A1 | 1/2008 | Dolezal et al. |
| 2008/0027480 A1 | 1/2008 | van der Burg et al. |
| 2008/0041373 A1 | 2/2008 | Doshi et al. |
| 2008/0163875 A1 | 7/2008 | Aarestad et al. |
| 2008/0183254 A1 | 7/2008 | Bly et al. |
| 2009/0270707 A1 | 10/2009 | Alfoqaha et al. |
| 2009/0276024 A1 | 11/2009 | Bonde et al. |
| 2009/0308395 A1 | 12/2009 | Lee et al. |
| 2009/0318986 A1 | 12/2009 | Alo et al. |
| 2009/0326408 A1 | 12/2009 | Moon et al. |
| 2010/0016749 A1 | 1/2010 | Atsma et al. |
| 2010/0036285 A1 | 2/2010 | Govari et al. |
| 2010/0047376 A1 | 2/2010 | Imbeau et al. |
| 2010/0076536 A1 | 3/2010 | Merz et al. |
| 2010/0094379 A1 | 4/2010 | Meadows et al. |
| 2010/0100150 A1 | 4/2010 | Kirby et al. |
| 2010/0125310 A1 | 5/2010 | Wilson et al. |
| 2010/0131029 A1 | 5/2010 | Durand et al. |
| 2010/0137931 A1 | 6/2010 | Hopper et al. |
| 2010/0137949 A1 | 6/2010 | Mazgalev et al. |
| 2010/0137956 A1 | 6/2010 | Osypka et al. |
| 2010/0152553 A1 | 6/2010 | Ujhazy et al. |
| 2010/0174341 A1 | 7/2010 | Bolea et al. |
| 2010/0228133 A1 | 9/2010 | Averina et al. |
| 2010/0228317 A1 | 9/2010 | Libbus et al. |
| 2010/0241207 A1 | 9/2010 | Bluger |
| 2010/0257729 A1 | 10/2010 | Alexander et al. |
| 2010/0262209 A1 | 10/2010 | King et al. |

FOREIGN PATENT DOCUMENTS

| | | |
|---|---|---|
| EP | 1 854 494 A1 | 11/2007 |
| JP | 53118893 | 10/1978 |
| JP | 9-294819 | 11/1997 |
| JP | 2000-506601 | 5/2000 |
| JP | 2000-508562 | 7/2000 |
| JP | 2003-305135 | 10/2003 |
| JP | 2004-508908 | 3/2004 |
| JP | 2004-532707 | 10/2004 |
| JP | 3688301 | 6/2005 |
| JP | 2005-521485 | 7/2005 |
| JP | 2007-21156 | 2/2007 |
| WO | WO 98/20938 | 5/1998 |
| WO | WO 02/24279 | 3/2002 |
| WO | WO 03/000133 | 1/2003 |
| WO | WO 03/000347 A1 | 1/2003 |
| WO | WO 03/082393 A1 | 10/2003 |
| WO | WO 2005/004993 A1 | 1/2005 |
| WO | WO 2006/045251 A1 | 5/2006 |
| WO | WO 2006/063339 A2 | 6/2006 |
| WO | WO 2007/134458 A1 | 11/2007 |

OTHER PUBLICATIONS

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

De Almeida et al., "Nasal pressure recordings to detect obstructive sleep apnea," *Sleep and Breathing*, Feb. 25, 2006, pp. 62-69, vol. 10 (2), Springer Heidelberg.

Saslow et al., "Work of breathing using high-flow nasal cannula in preterm infants," *Journal of Perinatology*, May 11, 2006, pp. 476-480, vol. 26 (8), Nature Publishing Group.

Campbell et al., "Nasal Continuous positive airway pressure from high flow cannula versus Infant Flow for preterm infants," *Journal of Perinatology*, Jul. 2006, pp. 546-549, vol. 26 (9), Nature Publishing Group.

Trevisanuto et al., "A new device for administration of continuous positive airway pressure in preterm infants: comparison with a standard nasal CPAP continuous positive airway pressure system" *Intensive Care Medicine*, Apr. 2005, pp. 859-864, vol. 31 (6), Springer-Verlag.

Verse et al., "New developments in the therapy of obstructive sleep apnea," *European Archives of Oto-Rhino-Laryngology*, Jan. 2001, pp. 31-37, vol. 258 (1), Springer-Verlag.

Paquereau et al., "Positive pressure titration in the treatment of obstructive sleep apnea syndrome using continuous airway positive pressure," *Revue Des Maladies Respiratoires*, Apr. 2000, pp. 459-465, vol. 17 (2), Masson Editeur.

Mahadevia et al., "Effects of expiratory positive airway pressure on sleep-induced respiratory abnormalities in patients with hypersomnia-sleep apnea syndrome," Am. Rev. Respir. Dis., Feb. 1983, vol. 128, pp. 708-711.

Tiran et al., "An Improved Device for Posterior Rhinomanometry to Measure Nasal Resistance," *Journal of Biomechanical Engineering*, Nov. 2005, vol. 127, pp. 994-997.

Noseda et al., "Compliance with nasal continuous positive airway pressure assessed with a pressure monitor: pattern of use and influence of sleep habits," Chest Clinics and Sleep Laboratories, Hôpitaux Erasme et Brugmann, Université Libre de Bruxelles, Brussels, Belgium, 2000, vol. 94, pp. 76-81.

Goding Jr. et al., "Relief of Upper Airway Obstruction With Hypoglossal Nerve Stimulation in the Canine," *The Laryngoscope*, Feb. 1998, pp. 162-169, vol. 108, Lippincott-Raven Publishers, U.S.A.

Sahin et al., "Chronic recordings of hypoglossal nerve activity in a dog model of upper airway obstruction," *Journal of Applied Physiology* 87(6), 1999, The American Physiological Society, pp. 2197-2206.

Ferguson et al., "Effect of Mandibular and Tongue Protrusion on Upper Airway Size During Wakefulness," *American Journal of Respiratory and Critical Care Medicine*, 1997, pp. 1748-1754, vol. 155.

Isono et al., "Interaction of cross-sectional area, driving pressure, and airflow of passive velopharynx," *American Physiological Society*, 1997, pp. 851-859, vol. 83.

Oliven et al., "Effect of genioglossus contraction on pharyngeal lumen and airflow in sleep apnoea patients," *European Respiratory Journal*, 2007, pp. 748-758, vol. 30, No. 4.

\* cited by examiner

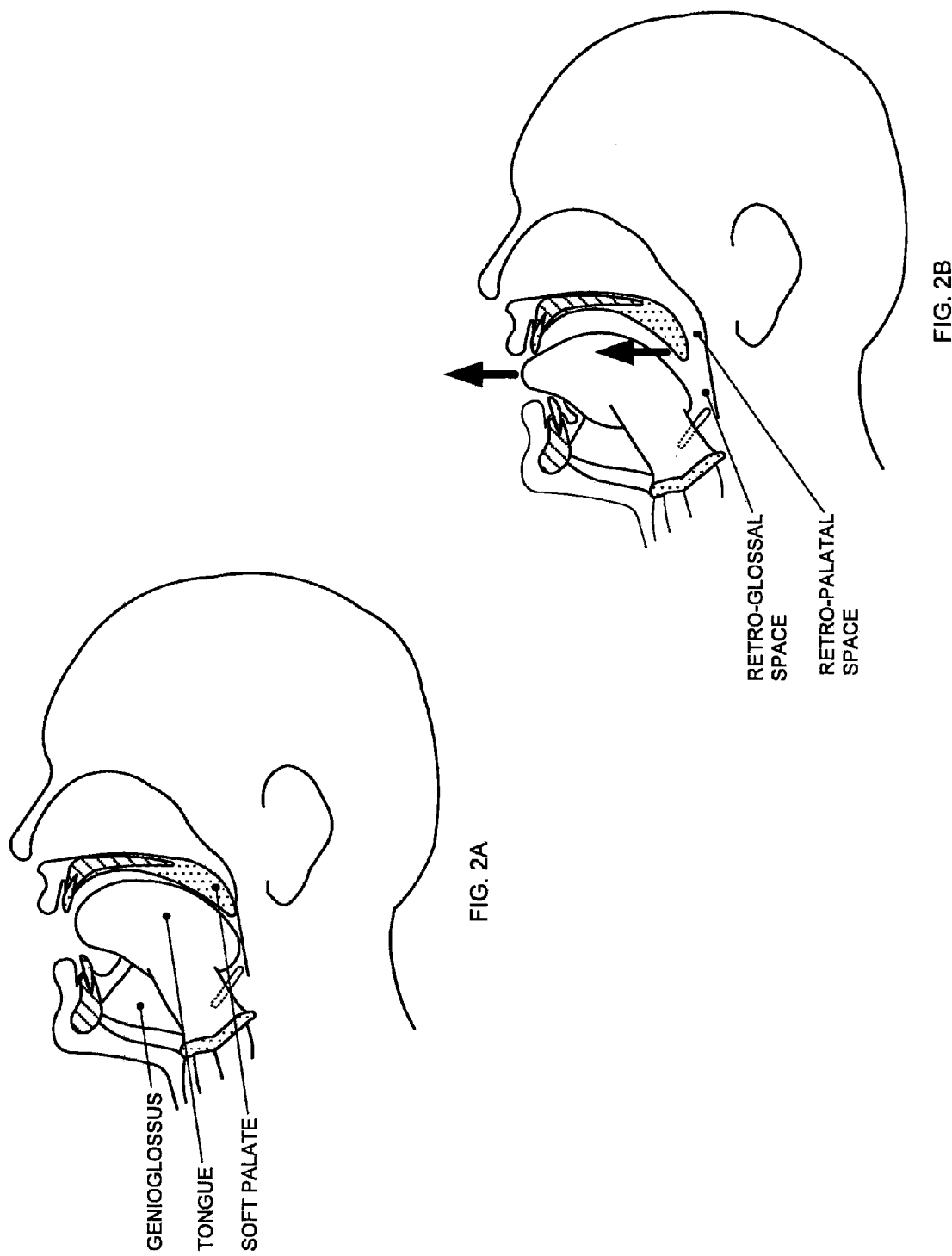

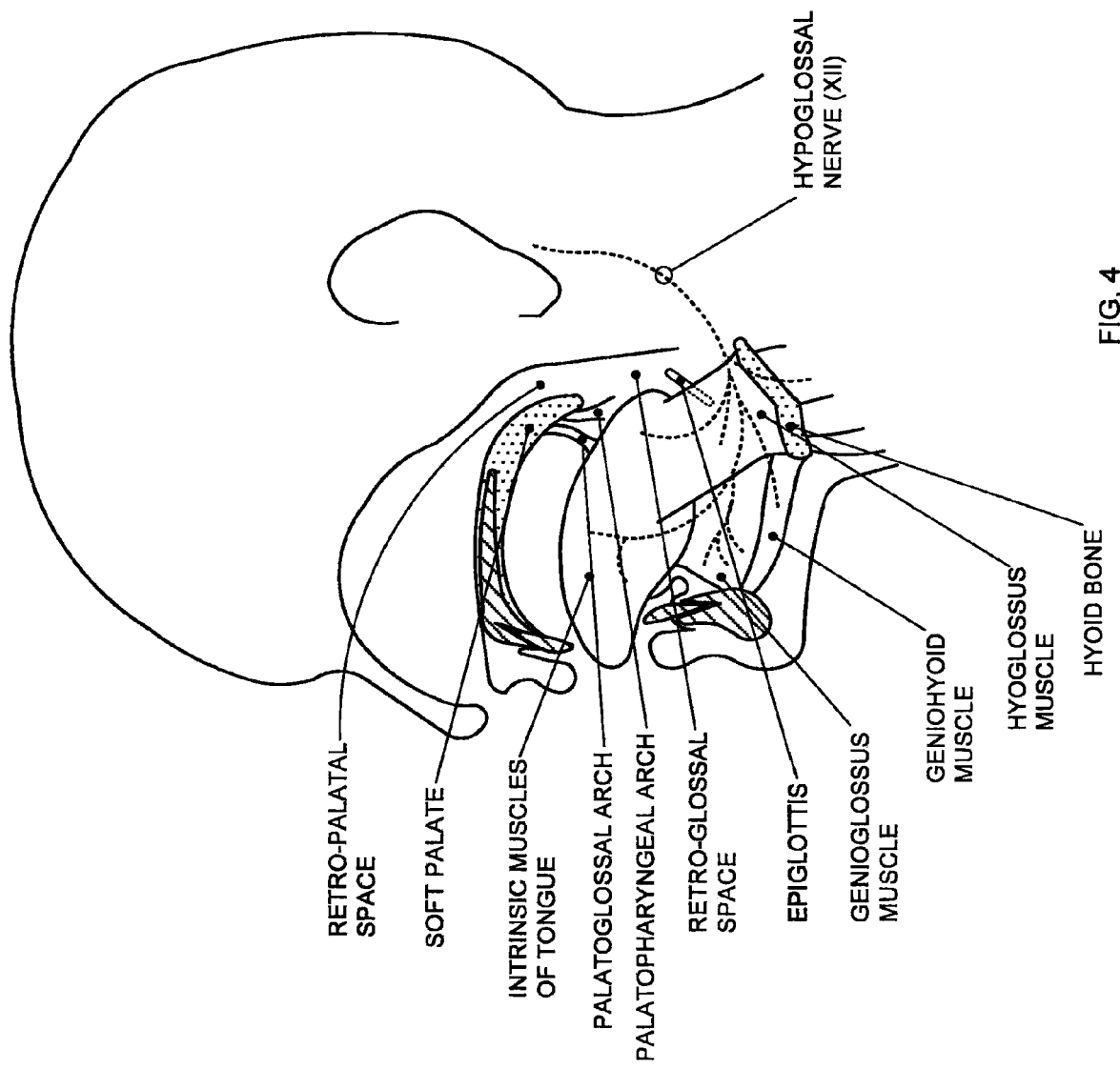

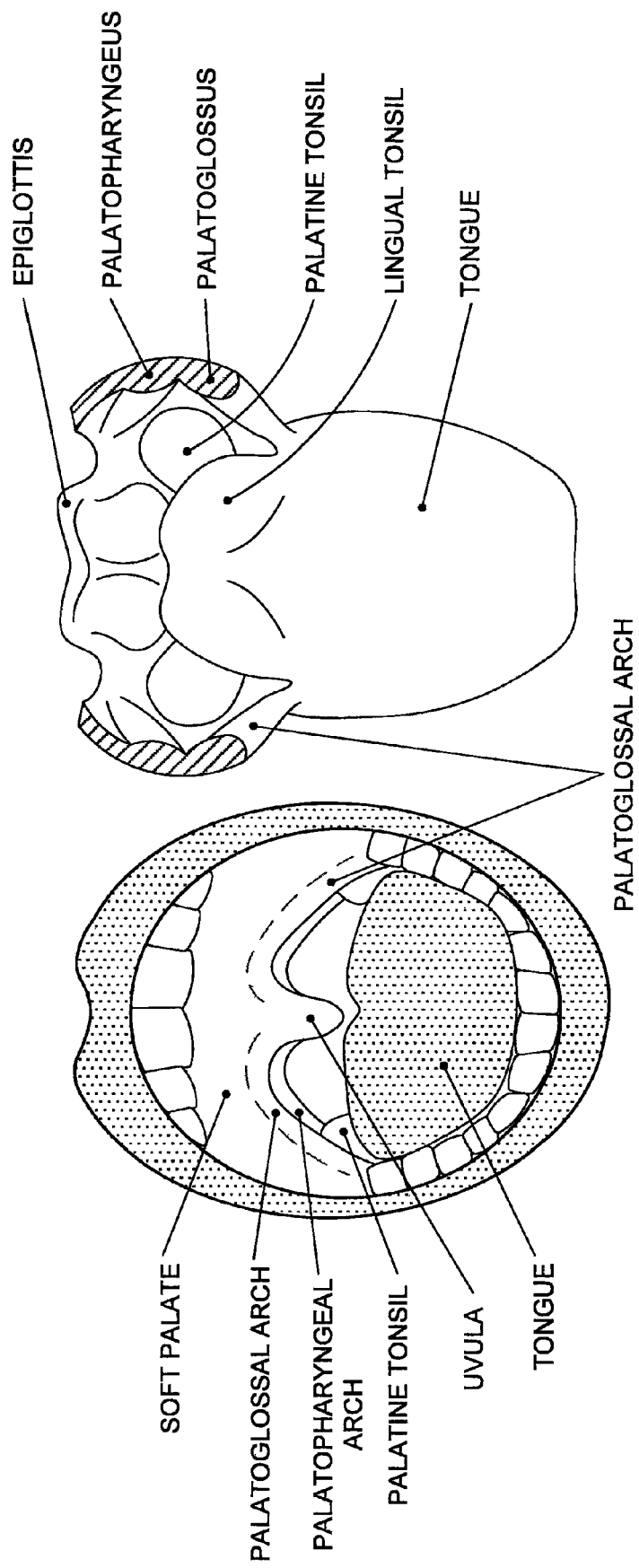

SCREENING DEVICES AND METHODS FOR OBSTRUCTIVE SLEEP APNEA THERAPY

CROSS REFERENCE TO RELATED APPLICATIONS

This patent application is a continuation of U.S. patent application Ser. No. 13/205,315, filed Aug. 8, 2011, entitled SCREENING DEVICES AND METHODS FOR OBSTRUCTIVE SLEEP APENA THERAPY, which is a continuation of U.S. patent application Ser. No. 13/113,524, filed on May. 23, 2011, entitled SCREENING DEVICES AND METHODS FOR OBSTRUCTIVE SLEEP APNEA THERAPY, which claims the benefits of priority under 35 U.S.C. §§119 and 120 to U.S. Provisional Patent Application No. 61/437,573, filed Jan. 28, 2011 entitled OBSTRUCTIVE SLEEP APNEA TREATMENT DEVICES, SYSTEMS AND METHODS, and U.S. Provisional Patent Application No. 61/467,758, filed Mar. 25, 2011, entitled SCREENING DEVICES AND METHODS FOR OBSTRUCTIVE SLEEP APNEA THERAPY. This patent application is related to U.S. patent application Ser. No. 13/106,460, filed May 12, 2011, entitled OBSTRUCTIVE SLEEP APNEA TREATMENT DEVICES, SYSTEMS AND METHODS to Bolea et al., which claims the benefit of U.S. Provisional Patent Application No. 61/437,573, filed Jan. 28, 2011, entitled OBSTRUCTIVE SLEEP APNEA TREATMENT DEVICES, SYSTEMS AND METHODS. This patent application also is related to U.S. patent application Ser. No. 13/251,856, filed October 3, 2011, now U.S. Pat. No. 8,386,046, entitled SCREENING DEVICES AND METHODS FOR OBSTRUCTIVE SLEEP APNEA THERAPY, which is a continuation of U.S. patent application Ser. No. 13/205,315, filed Aug. 8, 2011, entitled SCREENING DEVICES AND METHODS FOR OBSTRUCTIVE SLEEP APENA THERAPY, and to U.S. patent application Ser. No. 14/178,104, filed Feb. 11, 2014, entitled OBSTRUCTIVE SLEEP APNEA TREATMENT DEVICES, SYSTEMS AND METHODS, which is a continuation-in-part of U.S. patent application Ser. No. 13/205,315. The entire disclosures of each of the above-listed applications are incorporated herein by reference.

FIELD OF THE INVENTION

The inventions described herein relate to devices and methods for assessing and treating the upper airway. More particularly, the inventions described herein relate to devices and methods for assessing and treating the upper airway in patients with obstructive sleep apnea.

BACKGROUND OF THE INVENTION

Hypoglossal nerve stimulation has been proposed for the treatment of obstructive sleep apnea. An example of an implantable hypoglossal nerve stimulation system is described in U.S. Pat. No. 7,809,442 to Bolea et al. Published data suggest that response to hypoglossal nerve stimulation varies across subjects. Before undergoing a surgical procedure to implant a hypoglossal nerve stimulation system, it would be desirable to understand the likelihood of therapeutic success, and make clinical judgments accordingly.

SUMMARY OF THE INVENTION

To address this and other unmet needs, the present invention offers, in one example embodiment, a method for treating obstructive sleep apnea by first performing an assessment of the patient that involves observing the patient's upper airway during a tongue protrusion maneuver. The assessment may, for example, be done using endoscopy to observe the upper airway while the patient is awake in the supine position. The tongue protrusion maneuver may, for example, involve the patient volitionally protruding the tongue to its maximal extent with the mouth open or the lips loosely touching the tongue. The tongue protrusion maneuver mimics the effect of genioglossus activation by hypoglossal nerve stimulation (HGNS). Thus, an adequate increase in airway size during the tongue protrusion maneuver would be indicative of likely therapeutic success with HGNS. If the assessment shows an adequate increase in airway size during the maneuver, a HGNS device may be implanted in the patient with a higher confidence in a successful outcome. The principles of the present invention may be applied to other therapeutic interventions for OSA involving the upper airway.

BRIEF DESCRIPTION OF THE DRAWINGS

It is to be understood that both the foregoing summary and the following detailed description are provided by way of example, not limitation. Together with the following detailed description, the drawings illustrate example embodiments and serve to explain certain principles of the invention. In the drawings.

FIGS. 2A and 2B are schematic illustrations showing simplified structures of the upper airway in a lateral dissection with the palate and mandible shown in medial sagittal section;

FIG. 4 is a schematic illustration showing the structures of the upper airway in a lateral dissection with the palate and mandible shown in medial sagittal section;

FIG. 5 is a schematic illustration showing the structures of the upper airway from the oral cavity;

FIG. 6 is a schematic illustration showing isolated structures of the upper airway in a transverse section;

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
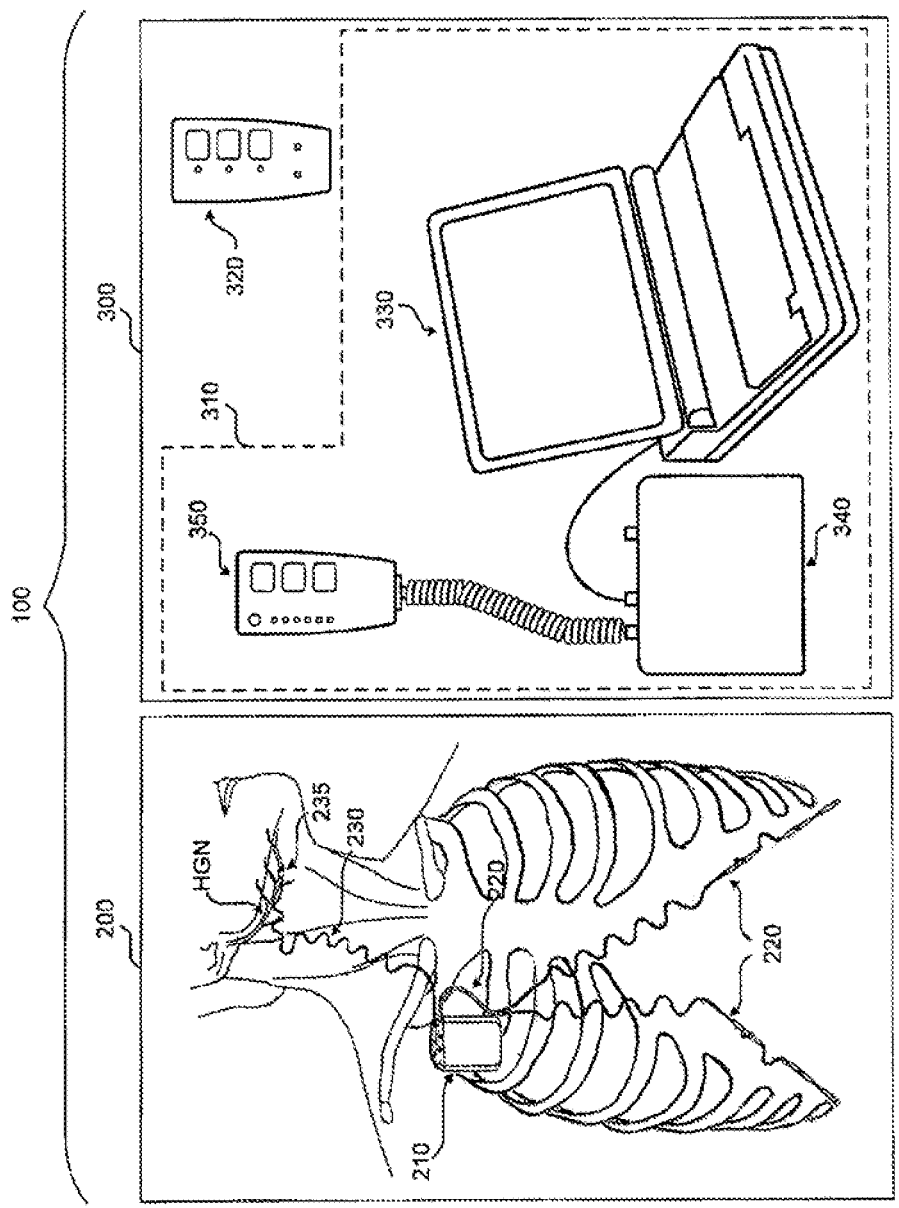
FIG. 1 is a schematic illustration of a hypoglossal nerve stimulation system.

FIG. 1 schematically illustrates a hypoglossal nerve stimulation (HGNS) system 100 comprising internal components 200 and external components 300. The HGNS system 100 is intended to treat obstructive sleep apnea (OSA) by increasing neuromuscular activity of the genioglossus muscle via stimulation of the hypoglossal nerve (HGN) synchronous with inspiration to mitigate upper airway collapse during sleep.

Stimulation is generated by an implantable neurostimulator (INS) 210, synchronized with inspiration as measured by the respiration sensing lead (RSL) 220 using bio-impedance, and delivered to the hypoglossal nerve by a stimulation lead (STL) 230. A programmer system 310 and a therapy controller 320 are wirelessly linked to the INS 210. The programmer system 310 includes a computer 330, a programmer interface 340, and a programmer head 350. The programmer system 310 is used by the physician to control and program the INS 210 during surgery and therapy titration, and the therapy controller 320 is used by the patient to control limited aspects of therapy delivery (e.g., start, stop, and pause).

The implanted components 200 of the HGNS system 100 include the INS 210, STL 230, and RSL 320. The INS is designed to accommodate one STL 230 and one RSL 220. One STL 230 may be used for unilateral implantation and unilateral hypoglossal nerve stimulation. Similarly, one RSL 220 may be used for respiration detection, and may be bifurcated as shown.

The implanted components 200 may be surgically implanted with the patient under general anesthesia. The INS 210 may be implanted in a subcutaneous pocket inferior to the clavicle over the pectoralis fascia. The distal end of the STL 230 (cuff 235) may be implanted on the hypoglossal nerve or a branch of the hypoglossal nerve in the submandibular region, and the proximal end of the STL 230 may be tunneled under the skin to the INS 210. The RSL 220 may be tunneled under the skin from the INS 210 to the rib cage and placed on both lateral sides of the costal margin. The INS 210 detects respiration via the RSL 220 using bio-impedance and stimulates the hypoglossal nerve via the STL 230 synchronous with inspiration.

Further aspects of the HGNS system 100 may be found in U.S. Provisional Patent Application No. 61/437,573, filed Jan. 28, 2011, entitled OBSTRUCTIVE SLEEP APNEA TREATMENT DEVICES, SYSTEMS AND METHODS, the entire disclosure of which is incorporated herein by reference. Patients with obstructive sleep apnea have repeated episodes of complete (apnea) or partial (hypopnea) upper airway collapse during sleep. The upper airway is generally defined by four walls: the posterior pharyngeal wall, the right and left lateral pharyngeal walls, and anteriorly, the soft palate and the tongue. The posterior pharyngeal wall is relatively fixed to the spinal column. Thus, collapse of the upper airway generally involves, depending on the level and mode of collapse, the tongue, the soft palate and/or the lateral walls. In rare cases, collapse may involve the nasopharynx and/or hypopharynx. As seen in FIG. 2A, the tongue and the soft palate have been displaced posteriorly, thus occluding the airway at the level of the tongue (retro-glossal collapse) and at the level of the soft palate (retro-palatal collapse). As seen in FIG. 2B, activation of the genioglossus muscle, for example by HGNS, causes anterior displacement of the tongue, thus opening the retro-glossal airway space. Activation of the genioglossus muscle can also cause anterior displacement of the soft palate, thus opening the retro-palatal airway space. Although not visible in this view, activation of the genioglossus muscle can further cause lateral displacement of the lateral pharyngeal walls, thus further opening the upper airway. In this manner, activation of the genioglossus muscle, for example by HGNS, can mitigate upper airway collapse in OSA subjects.

Although the effect of genioglossus activation on the tongue to open the retro-glossal airway is predictable given the mechanism of action, the effect of genioglossus activation on the soft palate and lateral walls has been heretofore poorly understood and variable across subjects. Nevertheless, in the majority of OSA patients, the soft palate and the lateral walls can contribute to upper airway collapse, alone or in combination with the tongue. Thus, observing these effects can be important to predicting the success of HGNS therapy. This is particularly true if the soft palate and/or lateral walls are known to contribute to airway collapse for a given OSA patient.

The present invention offers a method to mimic genioglossus activation to observe and assess the effects thereof on structures of the upper airway. The method generally involves causing the tongue to protrude while observing the response of the upper airway using an imaging technique. In general, the desired response is an increase in airway size. An adequate increase in airway size during the tongue protrusion maneuver is indicative of likely therapeutic success with HGNS. If an adequate increase in airway size is observed during the maneuver, a HGNS device may be implanted in the patient with a higher confidence of a successful outcome.

Figure 3B:
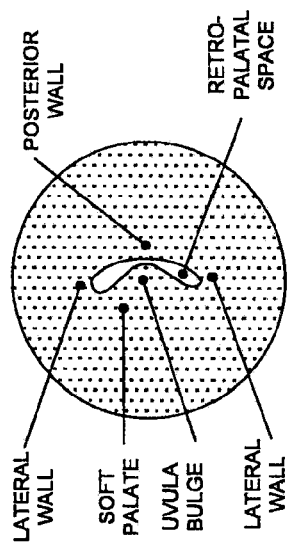
FIGS. 3B and 3C are views of the upper airway from the endoscope shown in FIG. 3A while the tongue is in a resting awake state (FIG. 3B) and during a tongue protrusion maneuver (FIG. 3C)
Figure 3C:
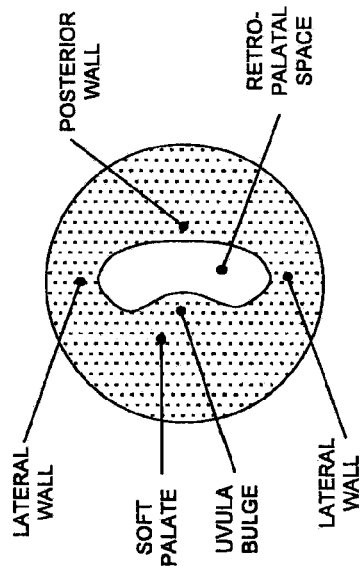
Figure 3A:
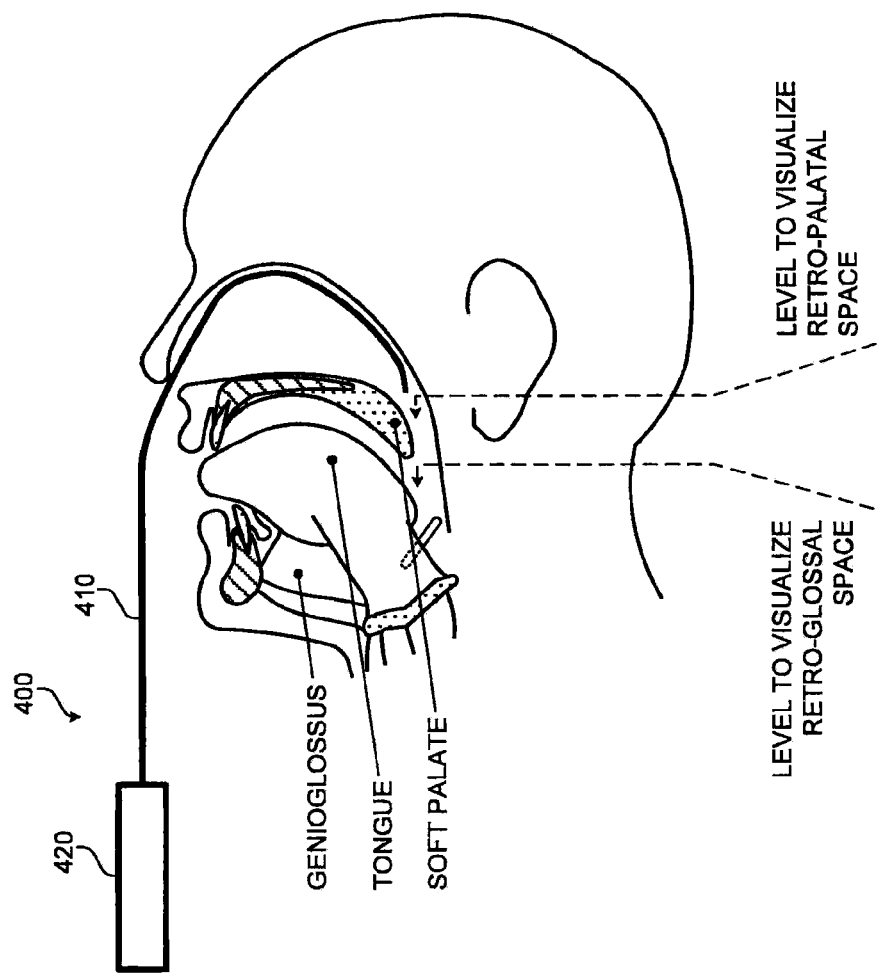
FIG. 3A is a schematic illustration showing an endoscope inserted into the airway

With reference to FIG. 3A, a naso-endoscope 400 may be used to visually observe the upper airway while the patient is awake in the supine position. Alternatively, the observation may be made while the patient is in a seated or semi-recumbent position. A conventional naso-endoscope 400 including a fiber optic shaft 410 and a hand piece 420 may be used. Hand piece 420 may include a light source and a viewing window, and/or facilitate connection to ancillary imaging equipment (e.g., light source, camera, monitor, recorder, etc.). The patient may be asked to volitionally protrude his/her tongue straight and to its maximal extent with the mouth open and the lips loosely touching the tongue. Alternatively, the tongue protrusion may be performed sub-maximally, which may limit muscle contraction to the genioglossus without recruiting other musculature. Also alternatively, the tongue protrusion may be performed by asking the patient to point the tip of the tongue to one side or the other, which may more closely mimic unilateral hypoglossal nerve stimulation. The distal end of the endoscope may be positioned superior to the soft palate and substantially parallel with the posterior pharyngeal wall to visualize the retro-palatal space. The distal end of the endoscope may be positioned inferior to the soft palate, superior to the tongue base and substantially parallel with the posterior pharyngeal wall to visualize the retro-glossal space. An example of the view of the retro-palatal upper airway space with the tongue in a relaxed (nominal) position is shown in FIG. 3B, and the same view with the tongue protruded is shown in FIG. 3C. As can be seen by comparing the views in FIGS. 3B and 3C, tongue protrusion can result in an increase in airway size, including area, circumference, anterior-posterior dimension, and lateral dimension. The increase in airway size at the level of the tongue and palate may be most discernable by an increase in anterior-posterior (AP) dimension between the posterior pharyngeal wall and the posterior side of the tongue base (retro-glossal) and soft palate (retro-palatal), respectively. Since the posterior pharyngeal wall is fixed relative to the spinal column, the increase in AP dimension involves anterior displacement of the tongue and soft palate, respectively. The increase in airway size may also be discernable by an increase in lateral dimension between the right and left lateral pharyngeal walls.

During the tongue protrusion maneuver, observing an adequate increase in size of the retro-glossal airway is predictive of HGNS efficacy in patients with isolated tongue base collapse. However, as mentioned above, the soft palate contributes to upper airway collapse in the majority of OSA patients, thus also observing an increase in size of the retro-palatal airway during the tongue protrusion maneuver is predictive of HGNS efficacy in patients with isolated soft palate collapse and combined tongue plus soft palate collapse.

By way of example, not limitation, the following procedure may be followed to conduct the assessment and tongue protrusion maneuver. With the patient awake in the supine position, a nasal endoscope is inserted into the pharynx via one of the nares to allow visualization of the upper airway. Video and still images may be captured at both the retro-palatal and retro-glossal levels to document the effect of different maneuvers on anatomic structures of the upper airway (tongue, palate, epiglottis, pharyngeal walls, etc.). When imaging the retro-palatal level, the endoscope may be placed such that all four walls (soft palate, posterior wall, and the two lateral walls) of the pharynx are visible before, during and after maneuvers. Similarly, when imaging the retro-glossal level, the endoscope may be placed such that all four walls (tongue base, posterior wall, and the two lateral walls) of the pharynx are visible before, during and after maneuvers. The endoscope may be placed such that it runs generally parallel to the posterior wall and provides a symmetric field of view. This may be achieved by initially placing the distal end of the endoscope near the level of the epiglottis and subsequently pulling back to the desired level. The patient then performs a series of maneuvers, including a tongue protrusion maneuver while breathing through his nose. The tongue protrusion maneuvers involves voluntary maximal straight tongue protrusion with lips loosely touching the tongue, with the mouth completely open, and/or with the teeth clenched closed. Other maneuvers such as a Mueller maneuver (inspiratory efforts against a closed airway) may be performed as well. Each maneuver is held for ≥2 seconds, and performed several times while data (images and measurements) are gathered.

Alternative non-volitional tongue protrusion maneuvers include, for example, manually gripping and pulling the tongue anteriorly (e.g., by the physician), using a tongue retaining device (e.g., as used for the treatment of OSA), both of which are non-invasive. Another alternative is to stretch the palatoglossal arch by pushing the tongue down (depress tongue), by pushing the arch laterally outward, or by pulling the arch anteriorly (all palatoglossal maneuvers) using a tongue depressor or similar device. The palatoglossal maneuver may be used in place of or in combination with the tongue protrusion maneuver, and the entire description herein with respect to the tongue protrusion maneuver is applicable to the palatoglossal maneuver. Other alternative non-volitional tongue protrusion maneuvers include, for example, sub-mental stimulation and intra-muscular stimulation (using fine wire electrodes, for example), both of which are relatively more invasive, but have the benefit of more selectively activating the genioglossus muscle alone to more closely mimic HGNS, as compared to volitional tongue protrusion which may recruit more than the genioglossus muscle.

Figure 3D:
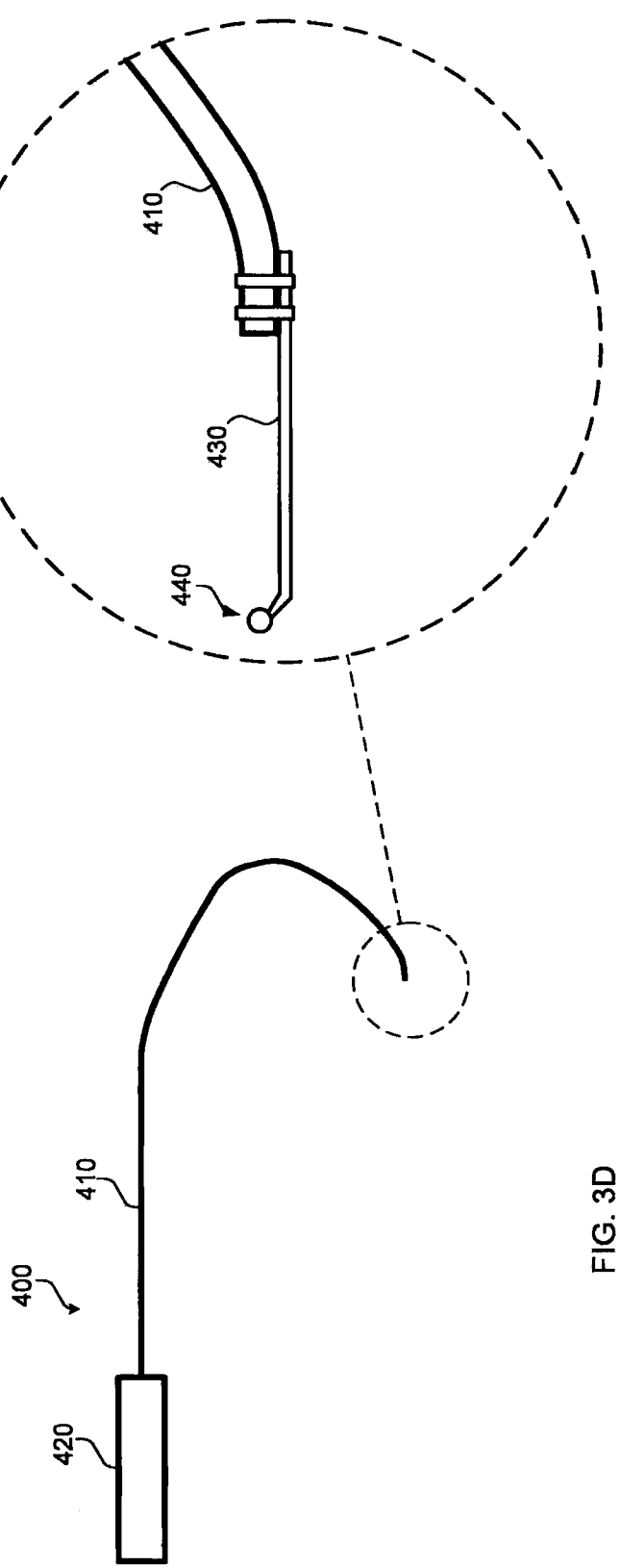
FIG. 3D is a schematic illustration of a modified endoscope.

Although naso-endoscopy is perhaps the most practical imaging technique to employ to assess the response of the upper airway to the tongue protrusion maneuver, other imaging techniques may be used as well. For example, x-ray imaging, fluoroscopy, x-ray computed tomography (CT), and optical coherence tomography (OCT) are suitable alternatives. These alternatives may provide more quantitative measurements by using a reference marker of known dimension in the field of view. Alternatively, improvements may be made to conventional naso-endoscopes to facilitate more quantitative measurements. For example, with reference to FIG. 3D, conventional naso-endoscope 400 includes a fiber optic shaft 410 and a hand piece 420. The distal end of the shaft 410 may include an attached extension 430 having a tip 440. The extension 430 positions the tip 440 into the field of view and may be approximated to the upper airway structure being visualized. The tip 440 may have a known dimension (e.g., diameter of 1 French or 3 mm), such that quantitative measurements of upper airway structures may be made by comparison. Other devices to make quantitative measurements may be employed, such as a laser pointer of know beam diameter projected onto the upper airway structure of interest. As an alternative, a catheter (e.g., nasogastric, nasoesophageal or nasopharyngeal catheter) may be inserted into the nasopharynx such that it resides in the field of view of the endoscope to serve as a quantitative reference of known dimension (e.g., diameter).

As mentioned above, the upper airway assessment during tongue protrusion maneuver may be used as a screening tool wherein the patient is treated with the desired therapy (e.g., HGNS) only if the increase in size of the upper airway meets a predefined criterion. To this end, the response of the upper airway may be measured using a qualitative scale such as a visual analog scale of 0-10, wherein 0 represents a closed airway and 10 represents a completely open or patent airway. The airway size may be scored with the tongue at rest and during the tongue protrusion maneuver. The patient may be treated if the difference between the two scores meets a threshold, if the score during the maneuver meets a threshold, or if both the difference between the scores and the score during the maneuver meet thresholds (e.g., 5 on a scale of 0-10).

Alternatively, the response of the upper airway may be measured using a quantitative scale such as: a pixel count of captured images which may be representative of cross-sectional area; a linear dimension such as anterior-posterior and/or lateral; or a measure of circumference. Here again, the airway size may be measured (e.g., pixel count, AP length, and/or lateral width) with the tongue at rest and during the tongue protrusion maneuver. The patient may be treated if the difference between the two measures meets a threshold, if the measure during the maneuver meets a threshold, or if both the difference in measures and the measure during the maneuver meet thresholds.

In each case, the threshold may be a percentage increase in size (e.g., difference in AP length=50%), an absolute value (e.g., difference of AP length=0.5 cm), or a relative value. The relative value may be with reference to an anatomical landmark such as the width of the superior aspect of the epiglottis (e.g., difference in AP length=50% of epiglottal width).

Other response criteria observed during the tongue protrusion maneuver, in addition to an increase in airway size, may be used as well. For example, movement of the hyoid bone may be observed visually, by palpation or by x-ray. Movement of the hyoid bone in an anterior direction and/or inferior direction during the tongue protrusion maneuver may be predictive of therapeutic success with HGNS.

As mentioned above, although the effect of HGNS and genioglossus activation on the tongue to open the retro-glossal airway is predictable given the mechanism of action, the effect of genioglossus activation on the soft palate and lateral walls has been heretofore poorly understood. The explanation lies in the mechanical linkages between the genioglossus and other pharyngeal structures defining the upper airway. The linkages are primarily muscular, and can be effective without independent activation. Nevertheless, it may be desirable to independently activate any one or a combination of the muscular structures described below by stimulating the muscle directly or by stimulating the corresponding motor nerve innervating the muscle.

With reference to FIG. 4, the mechanical linkages may be explained in more detail. By way of context, the hypoglossal nerve (cranial nerve XII) innervates the genioglossus muscle, which is the largest upper airway dilator muscle. Activation of the genioglossus muscle causes tongue protrusion and, in some cases, anterior displacement of the soft palate, due to linkage via the palatoglossal arch (muscle). Anterior displacement of the soft palate, in turn, can cause tension to be applied to the lateral pharyngeal walls via the palatopharyngeal arch (muscle), the effect of which is discussed in more detail below. Thus, activation of the genioglossus muscle causes opening of the upper airway at the level of the tongue base (retro-glossal space) and, in some cases, at the level of the soft palate (retro-palatal space). Because the linkage between the genioglossus and the soft palate via the palatoglossal arch varies across subjects, the response to HGNS at the level of the palate will vary as well. This is significant because most people with OSA have some involvement of the palate during obstructive events, and it may be helpful to identify those subjects with inadequate retro-palatal opening due to poor linkage (i.e., poor coupling) between the genioglossus and soft palate, possibly due to tissue redundancy (i.e., slack) in the palatoglossus. Tissue redundancy may also be present in the lateral pharyngeal walls due to the presence of adipose tissue (i.e., fat) at discrete locations (e.g., fat pads) or distributed throughout the pharyngeal walls, particularly in patients with high BMI.

Figure 7:
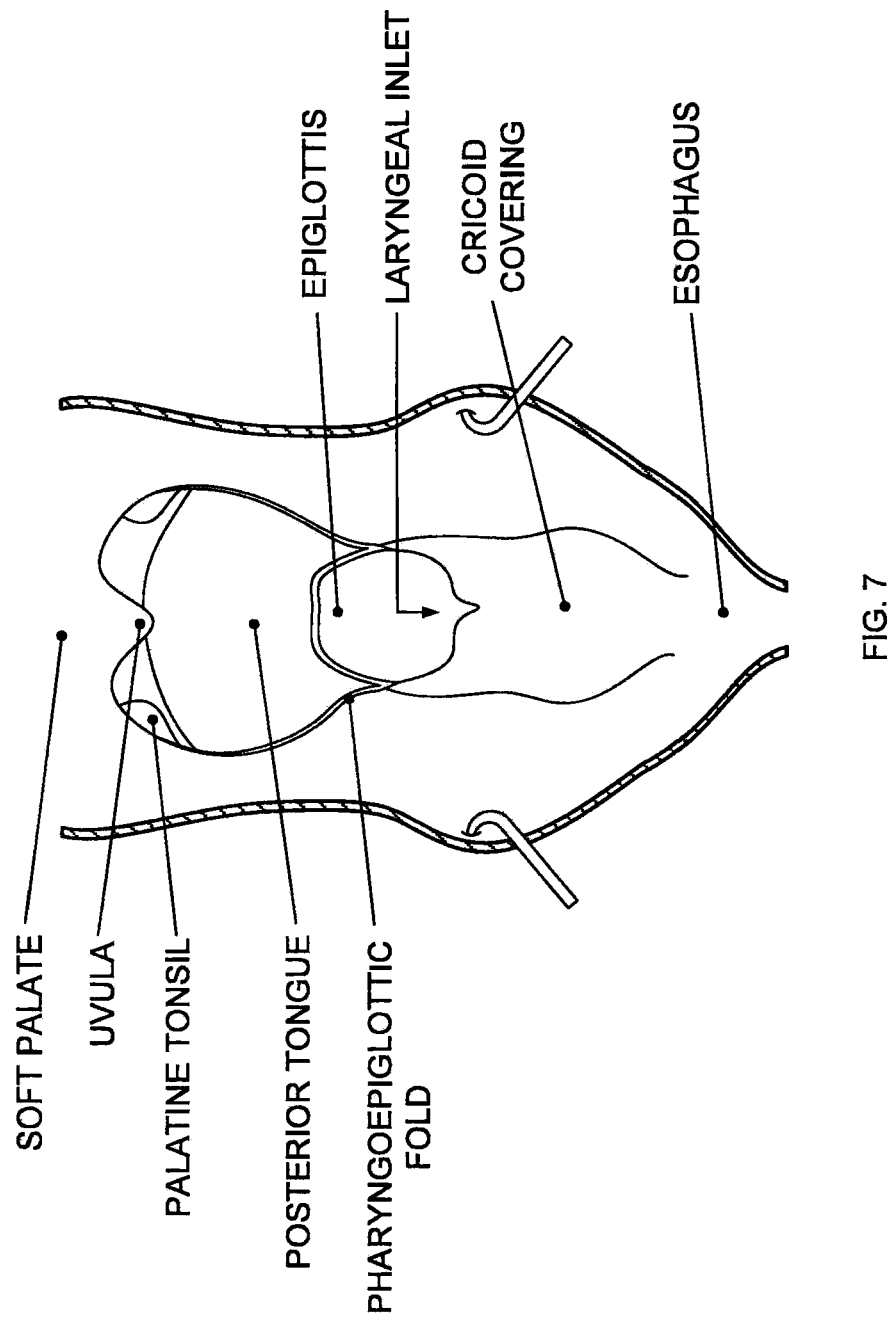
FIG. 7 is a schematic illustration showing structures of the upper airway in a posterior dissection of the interior pharynx.

The anatomical linkage between the tongue base (genioglossus) and the soft palate via the palatoglossal arch may be more clearly seen in FIGS. 5 and 6. The palatoglossus muscle forms the palatoglossal arch and the anterior-inferior aspect of the soft palate on either side of the uvula. The inferior and lateral ends of the palatoglossus muscle insert into the genioglossus muscle. Posterior to the palatoglossal arch are the palatine tonsils, and posterior to the palatine tonsils is the palatopharyngeus muscle forming the palatopharyngeal arch and the posterior-inferior aspect of the soft palate on either side of the uvula. The inferior and lateral ends of the palatopharyngeus muscle insert into the lateral walls of the pharynx. The soft palate is also linked to the lateral pharyngeal walls inferiorly via the pharyngoepiglottic fold as best seen in FIG. 7. Activation of the genioglossus serves to pull the soft palate anteriorly via the palatoglossal linkage. Anterior displacement of the soft palate serves to apply anterior and lateral (outward) tension to the lateral pharyngeal walls via the palatopharyngeal linkage as well as the inferior lateral pharyngeal walls via the pharyngoepiglottic linkage.

Figure 8:
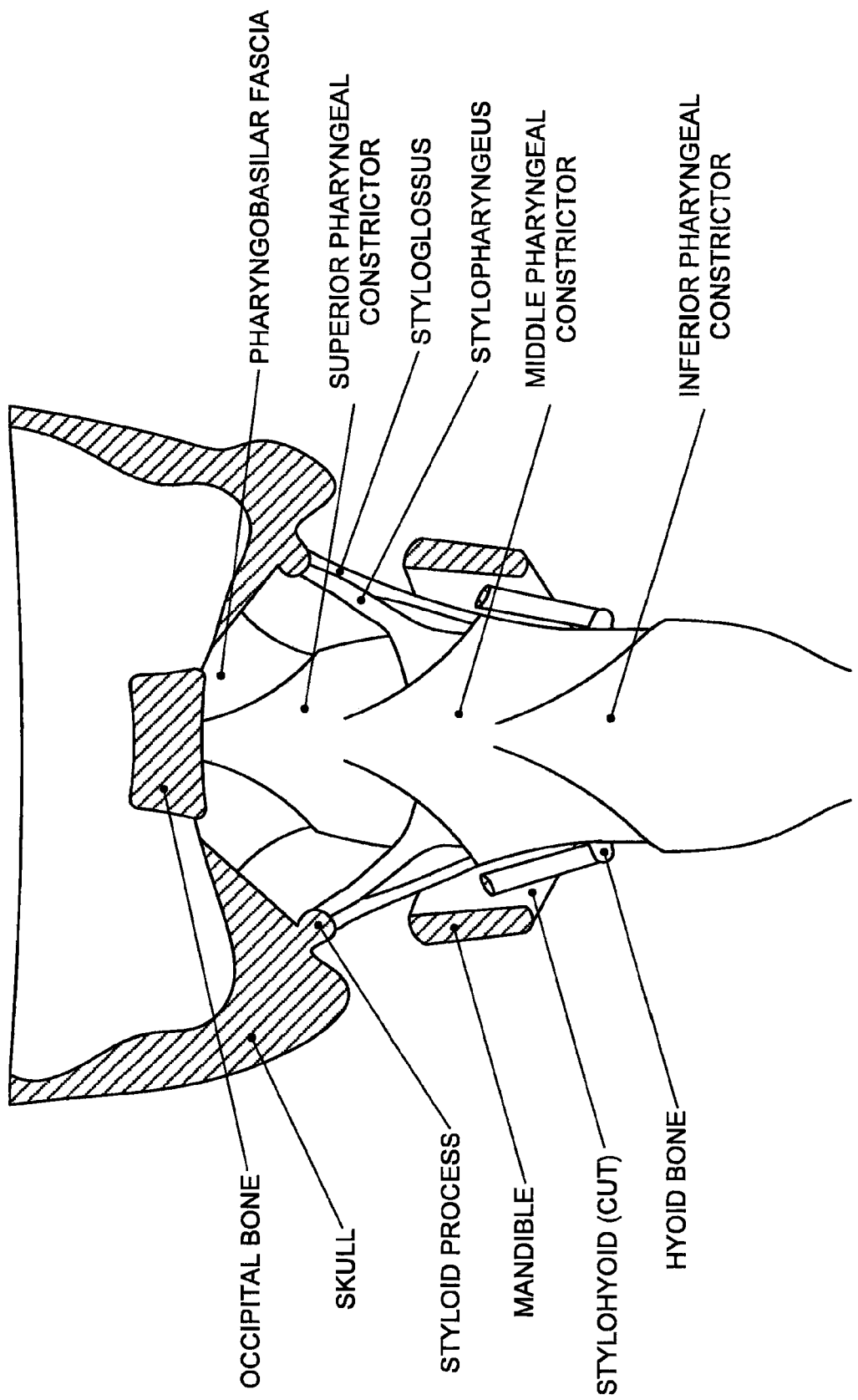
FIG. 8 is a schematic illustration showing structures of the upper airway in a posterior dissection of the exterior pharynx.

The anatomical linkage between the tongue base (genioglossus) and the lateral pharyngeal walls may be better appreciated with reference to FIG. 8. The anterior-inferior aspect (not visible) of the styloglossus muscles insert into the genioglossus, and the posterior-superior aspect of the styloglossus muscles attach to the styloid process. Similarly, the anterior-inferior aspect (not visible) of the stylopharyngeus muscles insert into the lateral pharyngeal walls, and the posterior-superior aspect of the stylopharyngeus muscles attach to the styloid process. The glossopharyngeal aspects of the superior pharyngeal constrictor muscle also insert into the genioglossus. Thus, activation of the genioglossus serves to apply tension to the styloglossus and the glossopharyngeal aspects of the superior pharyngeal constrictor muscle, which in turn apply lateral outward tension to the lateral pharyngeal walls by virtue of the lateral outward position of the styloid process and the linkage via the stylopharyngeus muscles.

In sum, activation of the genioglossus muscle opens the retro-glossal airway as well as the retro-palatal airway via the linkages described above. In addition, activation of the genioglossus muscle serves to open the lateral pharyngeal walls via the linkages described above. However, the linked effects on the soft palate and the lateral pharyngeal walls is not present in all subjects but may be important for therapeutic success of HGNS depending on the level and mode of collapse in a given patient. By using a tongue protrusion maneuver to mimic the effect on the genioglossus muscle seen with HGNS, the response of the soft palate and lateral walls may be observed using endoscopy, for example. If the palatal and lateral walls respond sufficiently to the tongue protrusion maneuver, the likelihood of successful treatment with HGNS increases. Thus, observing the response of upper airway structures to the tongue protrusion maneuver may be used as a screening tool prior to implantation of a HGNS device.

Optionally, it may be desirable to observe the response of the airway at the level of collapse. The level of collapse may be determined during sleep or simulated sleep (e.g. sedation) using known techniques such as drug induced sleep endoscopy (DISE), or may be determined by examination of the airway structures using known techniques such as naso-endoscopy. The airway may collapse at the level of the tongue base (i.e., retro-glossal), at the level of the palate (i.e. retro-palatal), or both levels. Because most OSA patients have palatal involvement in airway collapse, it may not be necessary to determine the level of collapse. In this case, collapse may be assumed to occur at least at the level of the palate, and therefore an adequate response (e.g., increase in airway size) in the retro-palatal space during the tongue protrusion maneuver would be indicative of likely therapeutic success with HGNS.

The principles of the present invention may be applied to other therapeutic interventions for OSA involving the upper airway. For example, the tongue protrusion maneuver may be used as a screening tool for surgery of the upper airway, such as uvulopalatopharyngoplasty (UPPP), palatal implants, genioglossus advancement, maxillo-mandibular advancement, etc. Also, the tongue protrusion maneuver may be used as a screening tool for oral appliances such as mandibular repositioning devices, tongue retaining devices, etc.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of assessing a patient's suitability for an upper airway stimulation therapy, the method comprising:
    observing with an imaging device whether the patient's airway experiences a collapse at the level of the patient's soft palate, the collapse comprising at least one of (i) the patient's soft palate moving towards the patient's posterior pharyngeal wall and (ii) the patient's left lateral pharyngeal wall moving towards the patient's right lateral pharyngeal wall; and
    receiving a criterion, the criterion concerning the patient's suitability for the upper airway stimulation therapy.

2. The method of claim 1, further comprising:
    instructing the patient to protrude the patient's tongue while observing a response of the patient's airway with the imaging device.

3. The method of claim 1, further comprising:
    protruding the patient's tongue without nerve stimulation while observing a response of the patient's airway with the imaging device.

4. The method of claim 1, wherein the observing takes place when the patient is subjected to drug-induced sleep endoscopy (DISE).

5. The method of claim 1, wherein the collapse is a complete collapse of the patient's airway.

6. The method of claim 5, wherein the observing takes place when the patient is subjected to drug-induced sleep endoscopy (DISE).

7. The method of claim 1, wherein the criterion corresponds to a recommendation that the upper airway stimulation therapy is not suitable for the patient.

8. The method of claim 1, further comprising:
observing an anatomical linkage between at least two of the patient's tongue, the patient's soft palate, the patient's left lateral pharyngeal wall, and the patient's right lateral pharyngeal wall.

9. The method of claim 1, wherein the observing of the airway includes observing movement of the patient's hyoid bone.

10. The method of claim 1, wherein the patient's airway is unpressurized during the observing with the imaging device.

11. A method of assessing a patient's suitability for an upper airway stimulation therapy, the method comprising:
recording with an imaging device a collapse of the patient's airway, the collapse comprising movements of the patient's soft palate towards the patient's posterior pharyngeal wall and the patient's left lateral pharyngeal wall towards the patient's right lateral pharyngeal wall;
recording a position of the patient's tongue during the collapse; and
generating a record of said recordings, wherein the record includes a magnitude of said movements,
wherein the record is configured for comparison to a criterion, the criterion concerning the patient's suitability for the upper airway stimulation therapy.

12. The method of claim 11, further comprising:
instructing the patient to protrude the patient's tongue while generating the record.

13. The method of claim 11, further comprising:
protruding the patient's tongue without nerve stimulation while generating the record.

14. The method of claim 11, wherein the record is generated when the patient is subjected to drug-induced sleep endoscopy (DISE).

15. The method of claim 11, wherein the collapse is a complete collapse of the patient's airway.

16. The method of claim 15, wherein the record is generated when the patient is subjected to drug-induced sleep endoscopy (DISE).

17. The method of claim 11, wherein the criterion corresponds to a recommendation that the upper airway stimulation therapy is not suitable for the patient.

18. The method of claim 11, further comprising:
documenting an anatomical linkage between at least two of the patient's tongue, the patient's soft palate, the patient's left lateral pharyngeal wall, and the patient's right lateral pharyngeal wall.

19. The method of claim 11, further comprising:
documenting a movement of the patient's hyoid bone.

20. A method of assessing a patient's suitability for an upper airway stimulation therapy, the method comprising:
providing a screening tool including a criterion, the criterion concerning the patient's suitability for the upper airway stimulation therapy, wherein the criterion is configured for comparison to observations made with an imaging device of the patient's airway during a collapse at the level of the patient's soft palate, the collapse comprising movements of the patient's soft palate towards the patient's posterior pharyngeal wall and the patient's left lateral pharyngeal wall towards the patient's right lateral pharyngeal wall.

* * * * *